United States Patent [19]

Zoels et al.

[11] Patent Number: 6,047,074
[45] Date of Patent: Apr. 4, 2000

[54] PROGRAMMABLE HEARING AID OPERABLE IN A MODE FOR TINNITUS THERAPY

[76] Inventors: Fred Zoels, Lettenfeldstr. 37, 90592, Altenhann; Ullrich Sigwanz, Buckenhofer Weg 39, 91058; Inga Holube, Anton Bruckner Str. 43, 91052, both of Erlangen; Raimund Martin, Klingenweg 3, 91330, Eggolsheim, all of Germany

[21] Appl. No.: 08/874,455

[22] Filed: Jun. 17, 1997

[30] Foreign Application Priority Data

Jul. 9, 1996 [EP] European Pat. Off. ............... 9611047

[51] Int. Cl.[7] .................................................. H04R 25/00
[52] U.S. Cl. ..................... 381/313; 381/73.1; 381/317; 381/314
[58] Field of Search ...................... 381/320, 321, 381/312, 314, 323, 73.1

[56] References Cited

U.S. PATENT DOCUMENTS

| | | | |
|---|---|---|---|
| 4,187,413 | 2/1980 | Moser | 381/320 |
| 4,680,798 | 7/1987 | Neumann | 381/68.4 |
| 5,014,319 | 5/1991 | Leibman | 381/320 |
| 5,167,236 | 12/1992 | Junker | 128/746 |
| 5,403,262 | 4/1995 | Gooch | 600/28 |
| 5,412,735 | 5/1995 | Engegretson | 381/320 |
| 5,604,812 | 2/1997 | Meyer | 381/314 |
| 5,636,285 | 6/1997 | Sauer | 381/314 |
| 5,721,783 | 2/1998 | Anderson | 381/68.6 |
| 5,892,836 | 10/1995 | Ishige | 381/320 |

FOREIGN PATENT DOCUMENTS

| | | |
|---|---|---|
| 0 415 677 | 3/1991 | European Pat. Off. . |
| 0415677 A2 | 3/1991 | European Pat. Off. ........ H04R 25/00 |
| OS 42 34 964 | 4/1994 | Germany . |
| OS 44 27 216 | 8/1996 | Germany . |
| 2 055 020 | 2/1981 | United Kingdom . |
| 2 234 349 | 2/1991 | United Kingdom . |
| 2235349 | 2/1991 | United Kingdom ........... H04R 25/00 |

OTHER PUBLICATIONS

"Advanced Digital Signal Processing Schemes for ITEs," Agnew, Hearing Instruments, vol., 42, No. 9 (1991), pp. 13, 14, 16, 17.

*Primary Examiner*—Paul Loomis
*Assistant Examiner*—Dionne N. Harvey

[57] ABSTRACT

A digital hearing aid is employable for tinnitus therapy, as well as for retraining tinnitus therapy, in combination with correction of other hearing impairments of a user of the hearing aid. For this purpose, the hearing aid contains a signal processing chain, between a hearing aid input and a hearing aid output, which is responsible for producing a useful signal by acting on the input signal in a manner to correct the hearing impairment of a user of the hearing aid. The signal processing chain also includes an arrangement for generating a tinnitus therapy signal, which is combined in the signal processing chain with the useful signal, dependent on a mode of operation which has been selected or set.

11 Claims, 4 Drawing Sheets

PROGRAMMABLE HEARING AID OPERABLE IN A MODE FOR TINNITUS THERAPY

BACKGROUND OF THE INVENTION

1. Field of the Invention

The present invention is directed to a programmable hearing aid of the type having at least one acoustoelectrical input transducer, a signal processing chain including a signal converter, an amplifier, a digital signal processor and a memory, and an electroacoustical output transducer.

2. Description of the Prior Art

A hearing aid of this type is disclosed in German Auslegeschrift 27 16 336, corresponding to U.S. Pat. No. 4,187,413. In this hearing aid, a microphone is provided as an input signal source that is connected to an amplifier followed by an analog-to-digital converter that is connected to a digital computer stag. A digital-to-analog converter is connected to the output of the computer stage and supplies an analog signal to an output amplifier to which an earphone is connected as an output transducer. The computer stage of this programmable hearing aid can be a microprocessor with a memory and can be implemented as an integrated module. A number of input signals, for example from a microphone and a pick-up induction coil, can thus be correlated with one another in the processor.

Tinnitus is a condition wherein a person perceives noises in the ear or head for which no external causes exist. This can be extremely uncomfortable and can lead to mental and physical disturbance in serious cases. The possibility of alleviating the tinnitus condition by drowning out the tinnitus noise with a sound signal supplied to the ear has been investigated for many years in the scientific literature.

PCT Application WO 90/07251 discloses a tinnitus masking device having an electronic circuit arranged in a housing and an earphone for generating a sound spectrum that can mask the tinnitus of the patient, with a volume control being provided for setting the sound intensity. In this device, the electronic circuit is fashioned such that the sound spectrum generated by the earphone contains a line spectrum with a fundamental tone, and the frequency of the fundamental tone can be set by the user. Tinnitus-masking devices can be either independent devices or can be built into a hearing aid, the combination of a tinnitus masker and a hearing aid being also referred to as tinnitus instrument. This instrument is employed given the appearance of tinnitus and simultaneous hearing loss, which occurs in a great percentage of tinnitus patients. These known devices operate with analog circuits for treating tinnitus or for tinnitus therapy. The tinnitus maskers generate a noise that can be individually adapted for every tinnitus patient in the limited framework to the patient's needs with respect to the frequency and level range. The goal of this therapy is to set the masking noise such that the patient no longer, or only barely, perceives the tinnitus and a more pleasant masking noise is audible instead.

A disadvantage of known tinnitus instruments is that the frequency range and the level range of the masking noise cannot be set with sufficient flexibility. Further, the known type of masking has the disadvantage that it is always in effect and the patient must manually shut the device off if the patient would like to hear normally in certain situations.

SUMMARY OF THE INVENTION

An object of the present invention is to provide a hearing aid of the type initially described which, without the aforementioned disadvantages, can also be utilized for tinnitus therapy.

These objects are achieved in a programmable digital hearing aid with at least one acoustoelectrical input transducer, a signal processing including a signal converter, an amplifier, a digital signal processor and a memory, and an electroacoustical output transducer in that the hearing aid, which is operable in a mode as a device for tinnitus therapy, by generating tinnitus therapy signals with the signal processor, for which the signal processor generates signals which can be combined with the digitized useful signal which is produced for correcting the hearing impairment (i.e., a hearing deficiency other than tinnitus) of the user.

With the hearing aid of the invention, the advantage of the integration of the tinnitus therapy is united in a digital hearing aid, thereby achieving high flexibility with respect to the frequency range as well as with respect to the level of the masking signals. Moreover, the hearing aid can be employed as a tinnitus masker as well as a tinnitus instrument or only as hearing aid, and various programs of the hearing aid can execute different functions dependent on the mode in which the user currently desires to operate the hearing aid. The programmed processing of the hearing aid can be very flexibly modified by replacement of the programming data without having to modify electrical components of the hearing aid. The inventive hearing aid is suitable for classic tinnitus therapy as well as for retraining therapy. Whereas classic tinnitus therapy requires a spectrally defined signal at moderate through high levels, significantly lower levels and broader band signals are used in the retraining therapy. The hearing aid of the invention enables a signal processing prescribable by various parameters, so that it executes different programs both as a hearing aid and as a tinnitus instrument. The programmability of the hearing aid offers the possibility of an adaptation to the hearing impairment and/or to the tinnitus condition of the patient and/or to the current auditory situation.

The use of a programmable hearing aid system makes it possible to generate nearly all desired signals for masking. The limitation to broadband noise is eliminated. This is especially advantageous in the case of tinnitus patients with normal hearing. The tone of the patient's tinnitus can be exactly identified and the corresponding frequency can be covered with narrowband noise. There is still the possibility in the selection of the signal to generate melodic sound sequences or other tones to mask the tinnitus, and thus the limitation of only generated noise is eliminated. Moreover, there is the possibility of automatically deactivating the masking signal when only hearing impairment correction is to be undertaken, and to activate it only given longer quiet pauses. This makes it possible for the hearing aid user to follow a conversation or to react to an acoustic signal without manually switching from masking to microphone mode. When a longer quiet pause occurs, then the masking signal is slowly mixed in and thus drowns out the disturbing tinnitus noise.

The invention provides the further possibility of analyzing the spectrum of the acoustoelectrical input signal of the hearing aid in real time and evaluating the signal part of the frequency range in which the tinnitus takes effect. If adequate level is present in the corresponding frequency range, then no masking signal is mixed in. If a threshold is downwardly transgressed, the masking signal is mixed in. A "blending" at the edges of the tinnitus frequency range is thus achieved.

The masking noises are generated, filtered and amplified in the signal processor of the digital hearing aid and are mixed into the signal path of the hearing aid between the input and the output transducers. Sine signals as well as narrowband noise with different center frequency, broadband noise and noise with variable frequency dependency can be generated in the signal processor. The selection of the signals ensues by the hearing aid acoustician or physician in consultation with the patient. The filtering and the amplification of the signals is also then set. The hearing aid can thus be employed for masking the tinnitus as well as for retraining therapy. Since the hearing aid allows a number of program settings, these can be perform different functions or modes (tinnitus masker, tinnitus instrument or hearing aid). This is advantageous since tinnitus can vary in intensity at different times of day or given different activities and a masking noise is therefore not always needed. A selection between a mode as a tinnitus masker or a mode as a tinnitus instrument and a hearing aid is of particular significance since it allows the masking signal to be deactivated. Moreover, the hearing aid of the invention can exhibit such a high sound quality that a tinnitus patient with normal hearing can wear it without deterioration of the sound quality. If the patient becomes no longer satisfied with the configuration of the device, then the hearing aid acoustician or the physician can undertake a re-adaptation on the basis of other parameter values that can be read into the memory of the hearing aid.

The following embodiments or developments are also possible with the hearing aid of the invention.

The level and/or the filtering of the masking signal can be varied by the patient by means of operating elements at the hearing aid.

The hearing aid can amplify the frequency range that is needed for influencing the tinnitus more than would be necessary due to the hearing loss, so that a masking effect can be achieved without additional masking signals. An additional dynamics compression can be provided to avoid transgression of a discomfort threshold.

The level of the masking signals can be variable dependent on the signal level.

A number of masking signals that are artificially generated or picked up in natural surroundings can be stored in the hearing aid. The tinnitus patient can select among these signals during ongoing hearing aid operation. These signals can be filtered as well as varied in level.

DESCRIPTION OF THE PREFERRED EMBODIMENTS

Figure 1:
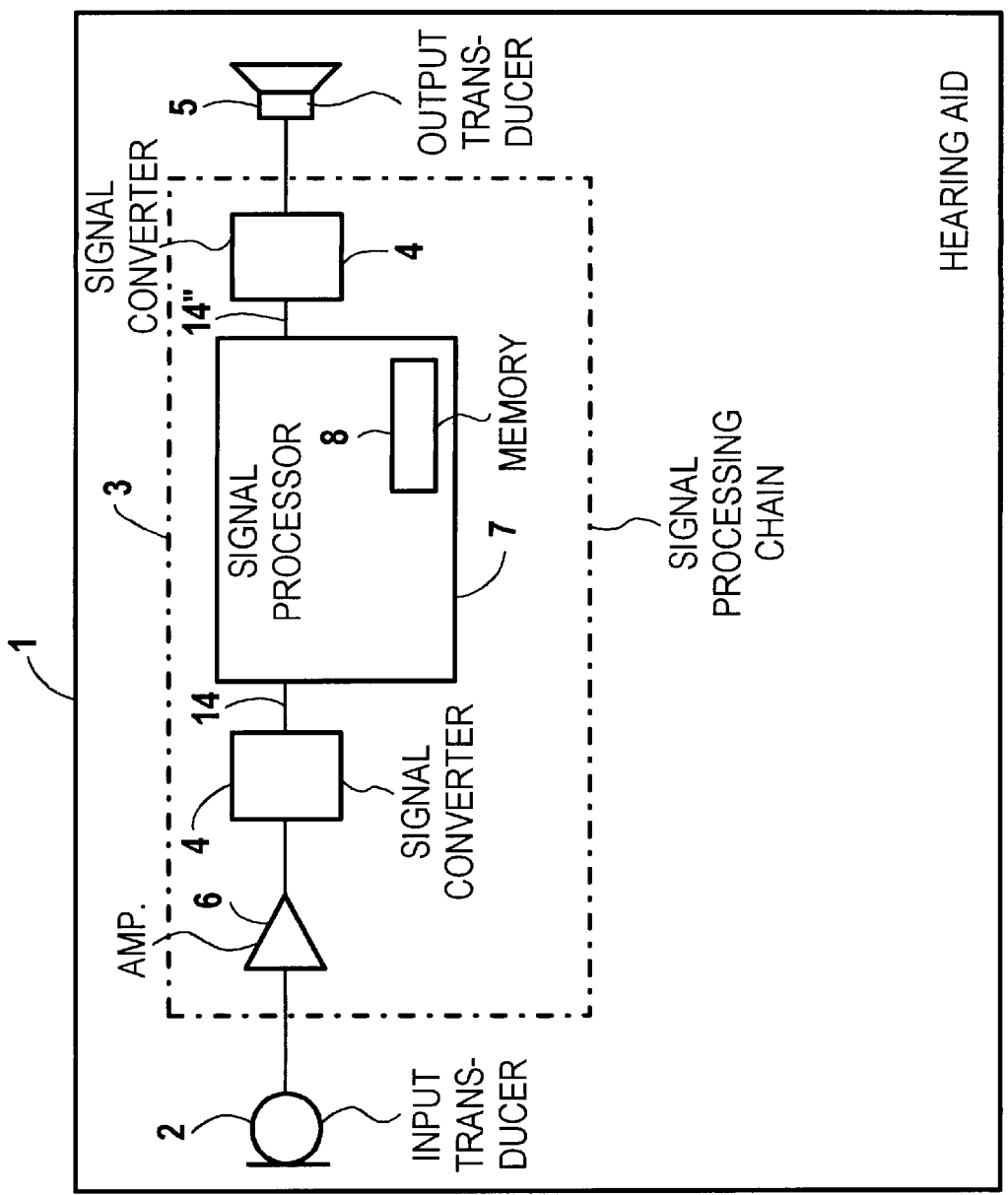
FIG. 1 is a block circuit diagram of a programmable, digital hearing aid constructed and operating in accordance with the principles of the present invention.

As shown in FIG. 1, a hearing aid 1 is composed of an input transducer 2, a signal processing chain 3 and an output transducer 5. The signal processing chain 3 includes, in particular, an amplifier 6, signal converter 4 and a signal processor 7. The signal processor 7 processes the digitized useful signal 14. A memory 8 is accessible by the signal processor 7.

According to the invention, such a digital hearing aid is employed for tinnitus therapy, whereby arbitrary signals can be generated in the signal processor 7 and combined with the digitized useful signal 14. Greater flexibility than with conventional analog hearing aids is thus achieved for tinnitus therapy. For example, a more detailed definition of the tinnitus is possible with respect to the frequency content, the level and/or the time structure, and an individual optimization of the signals for tinnitus therapy for a patient is possible with these improvements. Moreover, the device can be reprogrammed at any time given a change in the tinnitus or a change in the therapy without the patient needing a new hearing aid or parts of the hearing aid having to be replaced. The limitation of previous hearing aids of making use only of noise signals is eliminated since, for example, melodic sound sequences or other signals can also be generated. The combination of a device for tinnitus therapy with a digital hearing aid has the further advantage that this device can also be used for persons with normal hearing. A person with normal hearing can employ the digital hearing aid as a communication device that, for example given oversensitivity to loud useful signals, transforms these into a comfortable level range or reduces the unwanted noises present in the useful signal.

Figure 2:
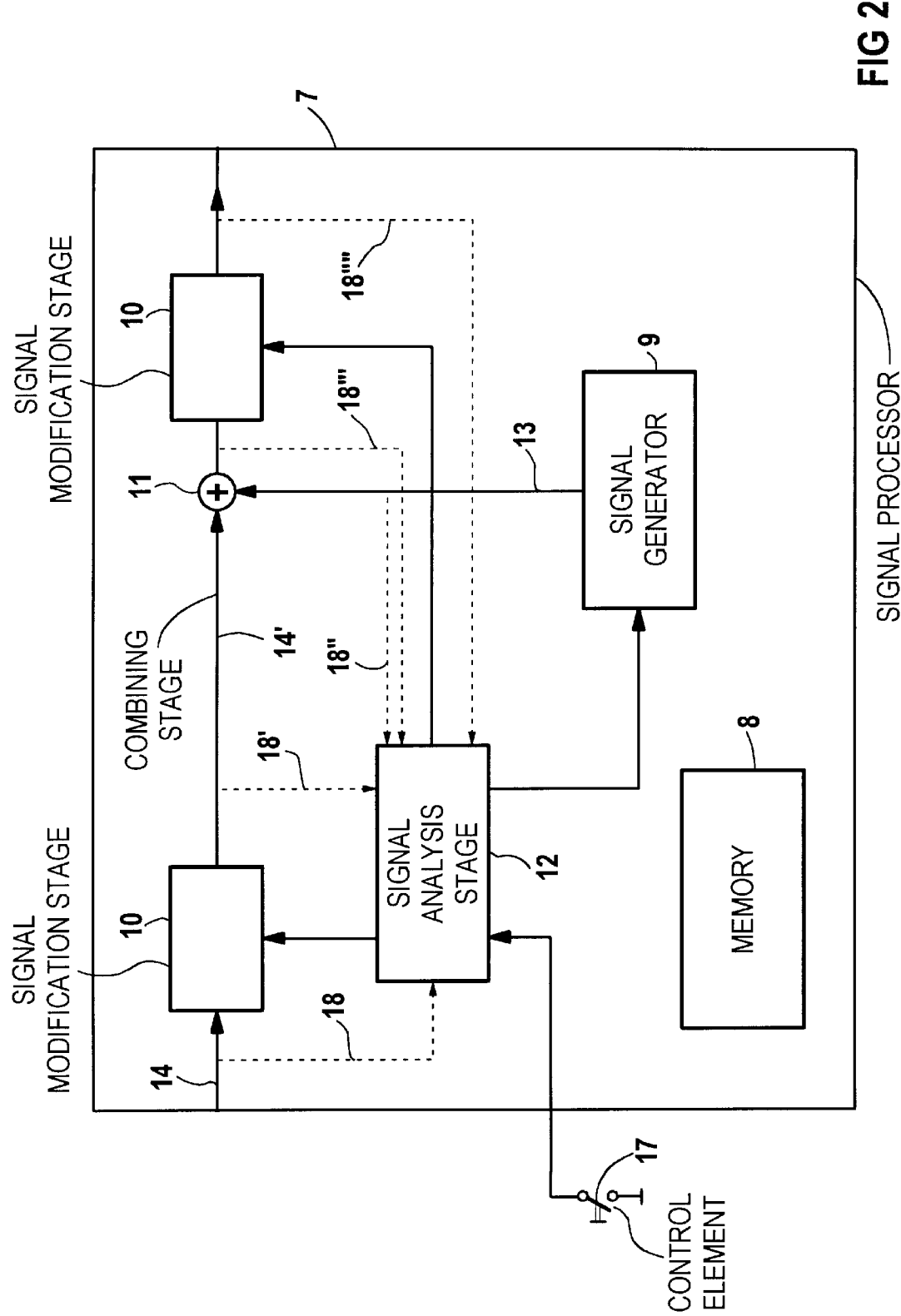
FIG. 2 is a block circuit diagram of a digital signal processor of an inventive hearing aid of FIG. 1.

FIG. 2 shows the structure of the signal processor 7. The digitized useful signal 14 is modified by signal modification stages 10. In addition to performing the usual functions of a digital hearing aid, signals 13 are produced by a signal generator 9 and are combined with the digitized useful signal 14' in a combining stage 11. The combination which takes place in the stage 11 can be not only addition, but also a modulation or the like. The signal processor 7 also contains a signal analysis stage 12. This stage 12 analyzes the digitized useful signals 14, 14', 14" and/or the signals from control elements 17 and controls the signal generator 9 and/or the signal modification stages 10 for influencing the useful signals therewith. To that end, the digitized useful signal is tapped at various locations 18, 18', 18", 18''', 18'''' of the signal processing chain 3. For example, this allows control of the signal generator 9 dependent on the digitized useful signal 14. The digital useful signal can be evaluated in terms of its intensity, its spectral distribution and/or its time structure and controls the signal generator 9 such that an oppositely directed (compensating) behavior can be achieved.

An advantage of such a control is, for example, that a constant correction of hearing impairment of the patient is possible without the useful signals being drowned out by the signals for tinnitus therapy since the signals for tinnitus therapy can be activated only when no useful signal is present. Arbitrary transition times between end of the useful signal and beginning of the signals for tinnitus therapy can thereby be set.

In this embodiment, an analysis of the spectrum of the digitized useful signals can be undertaken. If an adequately high signal level is present in the frequency range that is needed for the tinnitus therapy, then the signal generator 9 is not activated. If, however, an adjustable threshold is downwardly transgressed, then the signal 13 for tinnitus therapy is combined with the digitized useful signal 14'. A constant adaptation of the corresponding frequency range is thereby achieved.

According to an embodiment of the invention, the memory 8 can be employed for producing a time-dependent signal generation and/or signal variation programmed for the tinnitus therapy. Since tinnitus is often time-variable, the memory 8 can be programmed such that the signals for the tinnitus therapy also vary, for example dependent on the time of day, so that different signals are offered in the morning than in the evening, or the signals become increasingly softer at a time when the user is normally going to sleep, and then the signals are deactivated during the night.

Figure 3:
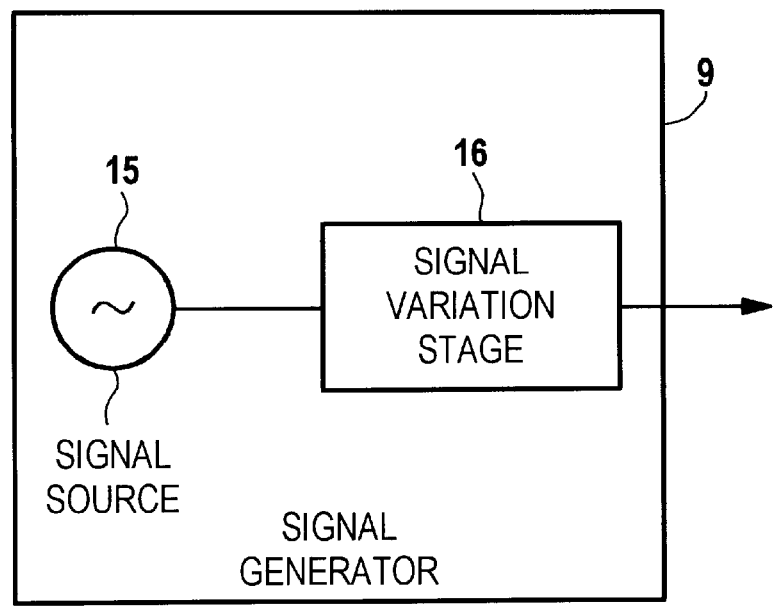
FIG. 3 is a block circuit diagram of a circuit for signal tinnitus therapy generation in the signal processor of the inventive hearing aid, that contains a signal source and a signal variation capability.
Figure 4:
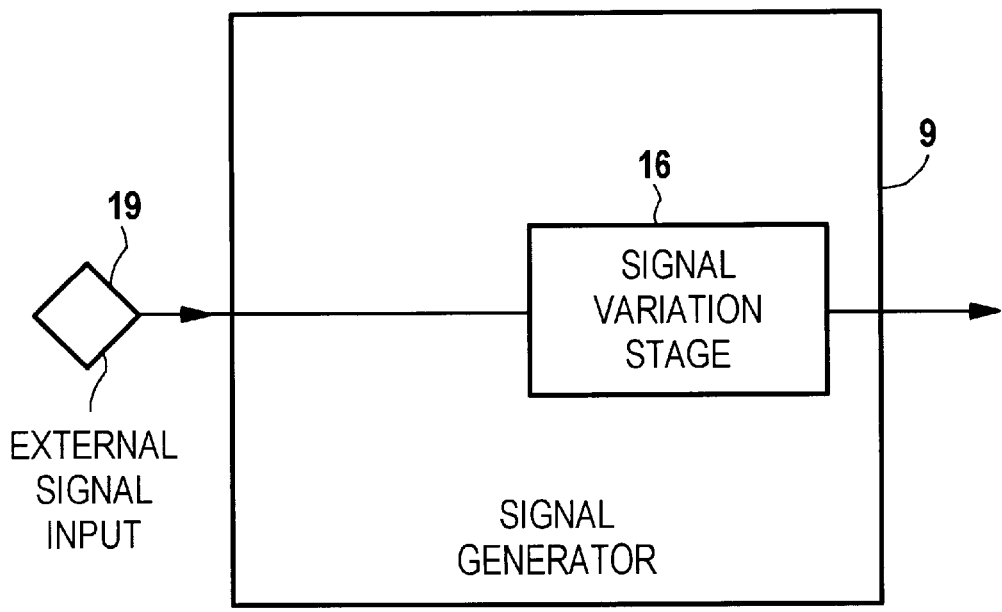
FIG. 4 is a block circuit diagram of a circuit for signal tinnitus therapy generation in the signal processor of the inventive hearing aid that has variation capability making use of externally supplied signals for tinnitus therapy.

According to a further modification of the invention, the patient can influence the level, the frequency content and/or the time structure of the signals for tinnitus therapy using the control elements 17 via the signal analysis stage 12, the generator 9 signal and/or a signal variation stage 16 in the signal generator 9 (see FIGS. 3 and 4). The patient can thereby optimize the setting for every situation. The selection of various programs by the patient is also advantageous, since these programs, for example, enable employment of the device as a hearing aid without signals for tinnitus therapy, as a device for generating signals for tinnitus therapy without combination with the useful signal, and/or as a combination of hearing aid with the signals for tinnitus therapy. This selection is advantageous since the signals for tinnitus therapy are not always needed or the useful signal is not always needed, dependent on the nature of the tinnitus, dependent on the therapy method or depending on the hearing impairment of the patient. In order to avoid the patient always receiving the same signal for tinnitus therapy, an automatic change or a manual change with the control elements 17, between different natural or technically generated signals for tinnitus therapy is possible. These signals are stored in the memory 8 and/or are fetchable via signal source 15 in the signal generator 9. As a result, an habituation effect to the signals can be avoided or diminished and irritation is also reduced.

Figure 5:
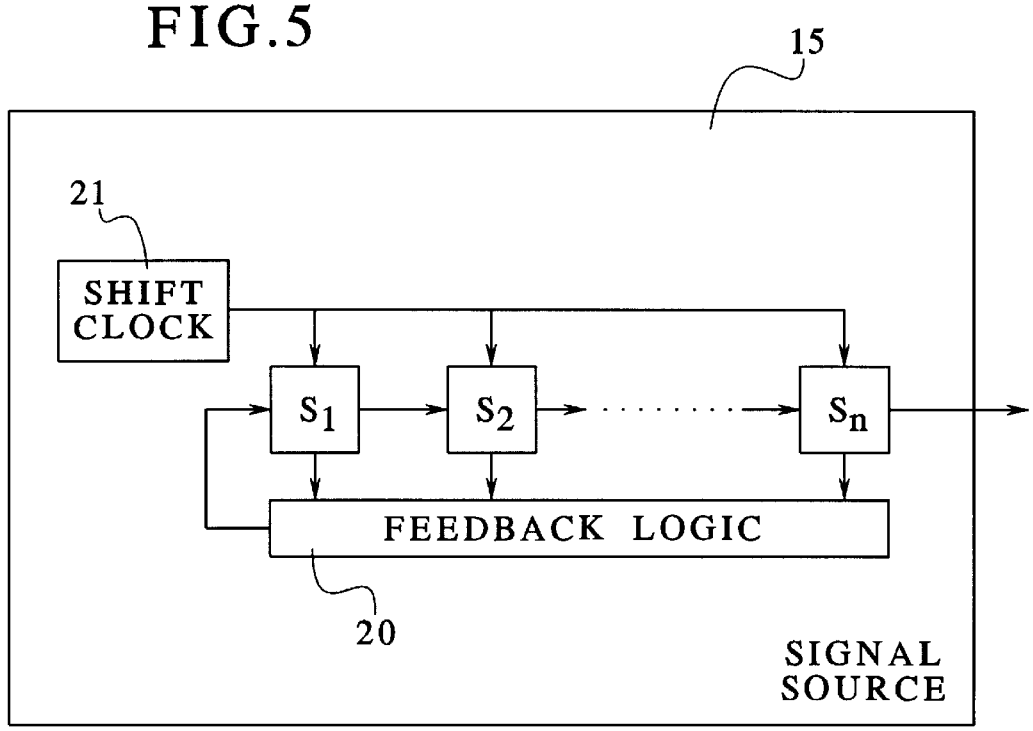
FIG 5 is a block diagram of a first embodiment of a signal source for use in a circuit for tinnitus therapy signal generation of the inventive hearing aid, using a shift register with feedback.
Figure 6:
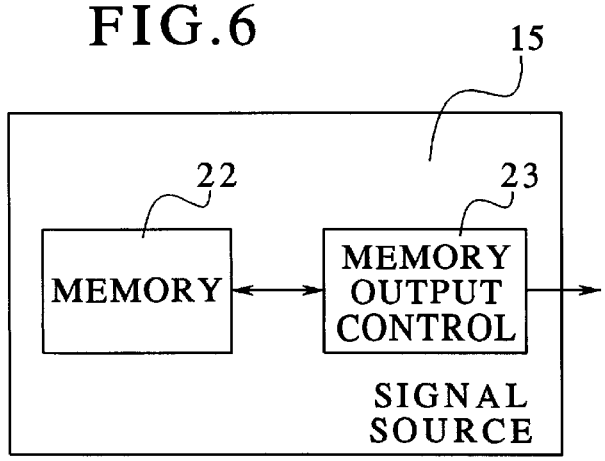
FIG. 6 is a block diagram of a second embodiment of a signal source for use in a circuit for tinnitus therapy signal generation of the inventive hearing aid, using a memory with controlled readout thereof.
Figure 7:
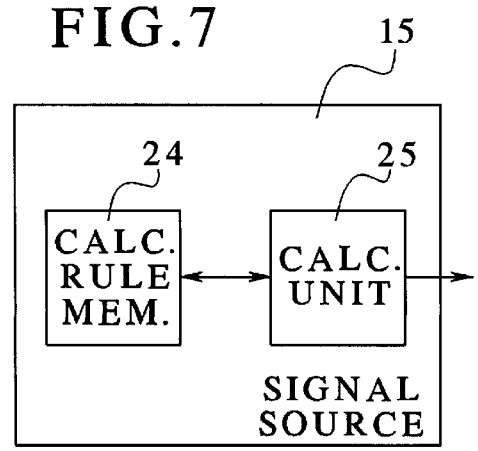
FIG. 7 is a block diagram of a third embodiment of a signal source for use in a circuit for tinnitus therapy signal generation of the inventive hearing aid, using stored calculating rules to generate a signal output.

FIG. 3 shows the structure of the signal generator 9 in detail. The signal generator 9 is composed of a signal source 15 and a signal variation stage 16. The signal source 15 can be composed of various embodiments. A first embodiment (FIG. 5) is a shift register composed of shift register stages $S_1 \ldots S_n$ operated by a shift clock 21, with feedback logic 20. A second embodiment (FIG. 6) can include a memory (which may be a part of the memory 8) in which digitized signals are stored and are readable therefrom via a memory output control 23. A third embodiment (FIG. 9) can be composed of calculating rules stored in a memory 24 supplied to a calculating unit 25 for generating signals. The digitized signals that are emitted by the signal source 15 are processed in the signal variation stage 16. They can thereby be shaped spectrally or in terms of time (time modulation) or can be influenced in terms of level. Any combination of these modifications can be used. The signals for tinnitus therapy thus can be individually set to the requirements for each patient. The limitations of an analog device are thereby overcome.

FIG. 4 shows a modification for the structure of the signal generator 9. This version also has a signal variation stage 16, but the signals are not generated by an internal signal source 15. Instead, the signals proceed into the device via an external signal input 19. For example, the external signal input 19 can be an audio input of the hearing aid or a receiver for AM or FM radio signals. By means of this external signal input 19, artificial or natural signals generated outside the hearing aid can be made available to the patient in an arbitrary processed form for tinnitus therapy.

Although modifications and changes may be suggested by those skilled in the art, it is the intention of the inventors to embody within the patent warranted hereon all changes and modifications as reasonably and properly come within the scope of their contribution to the art.

We claim as our invention:

1. A programmable hearing aid comprising:

an acoustoelectrical input transducer which emits an electrical analog input signal;

an analog-to-digital converter which converts said analog input signal into a digital input signal;

a digital signal processor supplied with said digital input signal, said digital signal processor having a signal path therein traversed by said digital input signal wherein said digital input signal is processed to produce a processed signal, said signal path having a plurality of signal taps at which tapped signals are respectively obtained;

a manually actuatable control element connected to said digital signal processor and, when actuated, supplying a first control signal thereto;

said digital signal processor including a signal analyzer which generates a second control signal dependent on at least one of said first control signal and said tapped signals;

said digital signal processor including means for generating a tinnitus therapy signal comprising a signal source which emits a signal source output, and means for varying said signal source output comprising means for at least one of spectrally shaping, time modulating and level influencing said signal source output dependent on said second control signal to generate said tinnitus therapy signal;

said digital signal processor including means for combining said processed signal and said tinnitus therapy signal to produce a processor output signal;

a digital-to-analog converter for converting said processor output signal into an electrical analog output signal; and an electroacoustic output transducer supplied with said analog output signal.

2. A programmable hearing aid as claimed in claim 1 wherein at least one of said signal taps precedes said means for combining.

3. A programmable hearing aid as claimed in claim 1 wherein at least one of said signal taps follows said means for combining.

4. A hearing aid as claimed in claim 1 wherein said signal source comprises a shift register with feedback.

5. A hearing aid as claimed in claim 1 wherein said signal source comprises memory means for storing a plurality of digitized signals, and means for reading out a selected one of said digitized signals, and wherein said second control signal identifies said selected one of said digitized signals.

6. A hearing aid as claimed in claim 1 wherein said signal source comprises memory means for storing a plurality of calculating rules and means employing said calculating rules in a selected manner for producing said signal source output signal, and wherein said second control signal identifies said selected manner of employing said calculating rules.

7. A hearing aid as claimed in claim 1 wherein said means for generating a tinnitus therapy signal comprises memory means for storing time-dependent control signals for adjusting said tinnitus therapy signal time-dependently.

8. A hearing aid as claimed in claim 1 wherein said means for combining said processed signal and said tinnitus therapy signal comprises an adder.

9. A hearing aid as claimed in claim 1 wherein said means for combining said processed signal and said tinnitus therapy signal comprises a modulator.

10. A hearing aid as claimed in claim 1 wherein said signal analyzer comprises means for analyzing said digital input signal and for modifying said digital input signal to produce characteristics in said processed signal opposite to characteristics in said tinnitus therapy signal.

11. A programmable hearing aid comprising:

an acoustoelectrical input transducer which emits an electrical analog input signal;

an analog-to-digital converter which converts said analog input signal into a digital input signal;

a digital signal processor supplied with said digital input signal, said digital signal processor having a signal path therein traversed by said digital input signal wherein said digital input signal is processed to produce a processed signal, said signal path having a plurality of signal taps at which tapped signals are respectively obtained;

said digital signal processor including a signal analyzer which generates a control signal dependent on said tapped signals;

said digital signal processor including means for generating a tinnitus therapy signal comprising an external connection adapted to receive an external signal, and means for varying said external signal comprising means for at least one of spectrally shaping, time modulating and level influencing said external signal dependent on said control signal to generate said tinnitus therapy signal;

said digital signal processor including means for combining said processed signal and said tinnitus therapy signal to produce a processor output signal;

a digital-to-analog converter for converting said processor output signal into an electrical analog output signal; and an electroacoustic output transducer supplied with said analog output signal.

* * * * *